(12) United States Patent
Parachur et al.

(10) Patent No.: US 10,813,910 B2
(45) Date of Patent: Oct. 27, 2020

(54) HERBAL COMPOSITION FOR THE TREATMENT OF AGE RELATED MACULAR DISEASES

(71) Applicant: Vivek Anand Parachur, Chennai (IN)

(72) Inventors: Vivek Anand Parachur, Chennai (IN); Somashekara Nirvanashetty, Chickmagalore (IN); Sripathy Ravichandran, Chennai (IN); Sanjib Kumar Panda, Chennai (IN)

(73) Assignee: Vivek Anand Parachur, Chennai (IN)

( * ) Notice: Subject to any disclaimer, the term of this patent is extended or adjusted under 35 U.S.C. 154(b) by 76 days.

(21) Appl. No.: 15/755,772

(22) PCT Filed: Aug. 24, 2016

(86) PCT No.: PCT/IN2016/050281
§ 371 (c)(1),
(2) Date: Feb. 27, 2018

(87) PCT Pub. No.: WO2017/033209
PCT Pub. Date: Mar. 2, 2017

(65) Prior Publication Data
US 2019/0160041 A1    May 30, 2019

(30) Foreign Application Priority Data
Aug. 25, 2015    (IN) .......................... 4464/CHE/2015

(51) Int. Cl.
| | | |
|---|---|---|
| A61K 36/00 | (2006.01) |
| A61K 36/28 | (2006.01) |
| A61K 36/48 | (2006.01) |
| A61K 31/353 | (2006.01) |
| A61K 36/9066 | (2006.01) |
| A61K 36/54 | (2006.01) |
| A61K 36/185 | (2006.01) |
| A61P 27/02 | (2006.01) |
| A61K 9/00 | (2006.01) |
| A61K 9/48 | (2006.01) |
| A61K 31/12 | (2006.01) |
| A61K 31/366 | (2006.01) |
| A61K 31/37 | (2006.01) |
| A61K 31/7048 | (2006.01) |
| A61K 36/18 | (2006.01) |
| A61K 39/395 | (2006.01) |
| A61K 47/18 | (2017.01) |
| A61K 47/22 | (2006.01) |
| A61K 47/24 | (2006.01) |
| A61K 47/32 | (2006.01) |
| A61K 47/38 | (2006.01) |
| C07K 16/22 | (2006.01) |

(52) U.S. Cl.
CPC .......... *A61K 31/353* (2013.01); *A61K 9/0048* (2013.01); *A61K 9/485* (2013.01); *A61K 9/4858* (2013.01); *A61K 9/4866* (2013.01); *A61K 31/12* (2013.01); *A61K 31/366* (2013.01); *A61K 31/37* (2013.01); *A61K 31/7048* (2013.01); *A61K 36/18* (2013.01); *A61K 36/185* (2013.01); *A61K 36/28* (2013.01); *A61K 36/48* (2013.01); *A61K 36/54* (2013.01); *A61K 36/9066* (2013.01); *A61K 39/3955* (2013.01); *A61K 47/18* (2013.01); *A61K 47/22* (2013.01); *A61K 47/24* (2013.01); *A61K 47/32* (2013.01); *A61K 47/38* (2013.01); *A61P 27/02* (2018.01); *C07K 16/22* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 8,163,312 B2 | 4/2012 | Krishnan et al. | |
| 2005/0249820 A1* | 11/2005 | Alam | A61K 8/671 424/638 |
| 2007/0031332 A1* | 2/2007 | Greenway | A61K 31/192 424/1.69 |
| 2015/0056255 A1* | 2/2015 | Ragot | A23F 5/36 424/401 |

OTHER PUBLICATIONS

Fernandez-Robredo, et al., "Current Treatment Limitations in Age-Related Macular Degeneration and Future Approaches Based on Cell Therapy and Tissue", Journal of Ophthalmology, vol. 2014, pp. 1-13.

Nowak, "Age-related macular degeneration (AMD): pathogenesis and therapy", Pharmacological Reports, 58, pp. 353-363 (2006).

* cited by examiner

*Primary Examiner* — Michael Barker
*Assistant Examiner* — Randall Winston
(74) *Attorney, Agent, or Firm* — Kramer Amado, PC

(57) ABSTRACT

The present invention discloses an herbal anti-AMD composition for treatment of age related macular diseases (AMD). More specifically, the present invention relates to an herbal composition for the prevention, management and treatment of neo-vascular or wet AMD.

6 Claims, 9 Drawing Sheets

HERBAL COMPOSITION FOR THE TREATMENT OF AGE RELATED MACULAR DISEASES

TECHNICAL FIELD OF THE INVENTION

The present invention relates to an herbal(s)/phytochemical (s) composition for the treatment of age related macular disease (AMD). More specifically, the present invention relates to an herbal (s)/phytochemical(s) composition for the prevention and treatment of neo-vascular or wet AMD. Further, the present invention relates to the present composition as an adjuvant for increasing the efficacy and/or decreasing the dose and/or decreasing the frequency/number of dose of existing preventive and treatment therapy.

BACKGROUND AND PRIOR ART OF THE INVENTION

Age related macular degeneration (ARMD or AMD) is a chronic eye disease having a potentially disabling consequence of causing blindness in individuals above the age of fifty and is observed commonly in individuals residing in industrialized nations. Macular degeneration involves deterioration in the central area of the retina, called the macula which plays an important role in regulating central vision, and is located in the inside back layer of the eyeball that converts light and images into electrical signals that are sent to the brain. AMD can occur in one or both eyes. The condition, which blurs central vision, is also called age-related macular degeneration due to its association with growing older. AMD is an inflammatory chronic progressive eye disease characterized by damage to retinal pigment epithelium (RPE) cells in its early stage, while late stage has two distinct forms: the slowly progressing nonvascular, also termed as atrophic or dry AMD and the rapidly progressing neo-vascular AMD, i.e. wet AMD (J. Z. Nowak, *Pharmacological Reports,* 58, 3, 353-63, 2006.). Wet or neovascular AMD affects approximately 10-15% of individuals with age-related macular degeneration, but accounts for approximately 90% of all cases of severe vision loss from the disease.

Wet age-related macular degeneration, is characterized by the proliferation of abnormal blood vessels under the retina towards the macula. Since these blood vessels are abnormal, they tend to break, bleed, and leak fluid, thereby damaging the macula and causing it to lift up and pull away from its base. This can result in a rapid and severe loss of central vision. Although the epidemiology of AMD is not known, several new treatments are available for wet age-related macular degeneration.

Conventional therapeutic methods targeting degenerative diseases have been largely centred on palliative forms of treatment that mainly alleviate and control symptoms of a disease without addressing the underlying biological cause. Presently there is no cure available for AMD, and even palliative treatments are rare. Treatment options comprise a broad range of therapeutic approaches, including thermal laser photocoagulation, surgical approaches and new treatments targeting the choroidal neovascularization (CNV) component and its pathogenic cascade, such as verteporfin with photodynamic therapy (vPDT) and more recently anti-vascular endothelial growth factor (VEGF) therapies (P. Fernández-Robredo et al *Journal of Ophthalmology Volume* 2014).

The vascular endothelial growth factor (VEGF) is a potent stimulator of angiogenesis and its role in the pathogenesis of neovascular AMD has been well documented. Patients diagnosed with neovascular AMD can be only symptomatically treated with a few known VEGF inhibitors that are effective in preventing the progression of vascular AMD. Monthly injections of Ranibizumab or Bevacizumab are the current, standard therapies in the management of neovascular AMD. However, it has been indicated that Bevacizumab, even though not an exorbitantly priced drug, its accumulation within retinal pigment epithelial cells, possibly induces long-term side-effects. Furthermore, Ranibizumab is expensive with costs of around 2000 USD per injection.

U.S. Pat. No. 8,163,312 relates to herbal formulation comprising *Curcuma longa, Terminalia chebula* and *Acacia catechu* amongst several other herbal ingredients for prevention and treatment of diabetes and associated complications. The composition is said to prevent retinal damages, cataract and deterioration of vision usually associated with diabetes. However, the composition featured therein does not represent any treatment measure for neovascular AMD. Moreover, the herbal composition disclosed therein does not demonstrate any inhibitory activity against VEGF. No attempts have been made in US'312 to describe the synergistic effect of the herbal ingredients used therein.

In view of the need to consider the safety as well as the cost-effectiveness for formulating treatment and preventive measures, the present inventors have devised an herbal composition for the prevention and treatment of neo-vascular AMD.

SUMMARY OF THE INVENTION

In an aspect, the present invention provides an herbal anti-AMD (Age related Macular Diseases) composition comprising (a) one or more standardized herbal extract (s) selected from the group consisting of *Cinnamomum verum, Terminalia chebula,* and *Acacia catechu* in concentrations constituting about 30% to about 50% of the present composition;
(b) one or more standardized herbal extract (s) selected from the group consisting of *Silybum marianum,* and *Curcuma longa* in concentrations constituting about 20% to about 40% of the present herbal composition; and
(c) a standardized extract of *Punica granatum* constituting about 1% to about 10% of the present herbal composition.

Accordingly, the herbal composition comprises extracts comprising standardized concentrations of phytochemicals having concentrations of 2 to 8% procyanidin from *Cinnamon verum,* 8 to 25% chebulagic acid and 15 to 30% chebulinic acid obtained from *Terminalia chebula;* 0.2 to 3% of catechin from *Acacia catechu,* 60 to 80% of silymarin from *Sylibum marianum,* 35% to 100% of curcumin and/or curcuminoids from *Curcuma longa,* and 1 to 25% of ellagic acid from *Punica granatum.* Generally these extract may contain higher amount of total polyphenolic content in addition to these active ingredients.

In another aspect, the present invention provides an herbal composition for the prevention and/or stabilization, management and treatment of visual acuity loss due to Age Related Macular Degeneration (AMD), specifically wet AMD.

Additionally, the present herbal composition is also employed in the prevention and/or stabilization, management and treatment of diabetic macular edema (DME) and retinal vein occlusion (RVO).

Further, the present composition may be used either in adjunct therapy and/combination therapy for intravitreal anti-VEGF injections, ophthalmic or topical and oral dosage forms. Accordingly, one more aspect of the present invention relates to the present herbal composition along with one or more pharmaceutically acceptable excipients for use in oral and ophthalmic formulations.

In one aspect, the present invention provides a method of treatment of age related macular diseases in diseased individuals comprising administering a therapeutically effective concentration of the present herbal anti-AMD composition to a subject in need thereof.

The present composition can be used for reducing the frequency and/or dose of intravitreal injections containing VFGF inhibitors such as Bevacizumab, Ranibizumab and aptamer/antibody directed against platelet-derived growth factor either alone or in combination.

Furthermore, the present composition can be used for enhancing/increasing therapeutic efficacy of intravitreal injections containing VFGF inhibitors such as Bevacizumab, Ranibizumab and aptamer/antibody directed against platelet-derived growth factor either alone or in combination.

In yet another aspect, the present invention provides an herbal anti-AMD composition with higher bioavailability to facilitate crossing of the bioactive ingredients across the blood and retinal barrier.

SOURCE OF BIOLOGICAL MATERIAL

Figure 1:
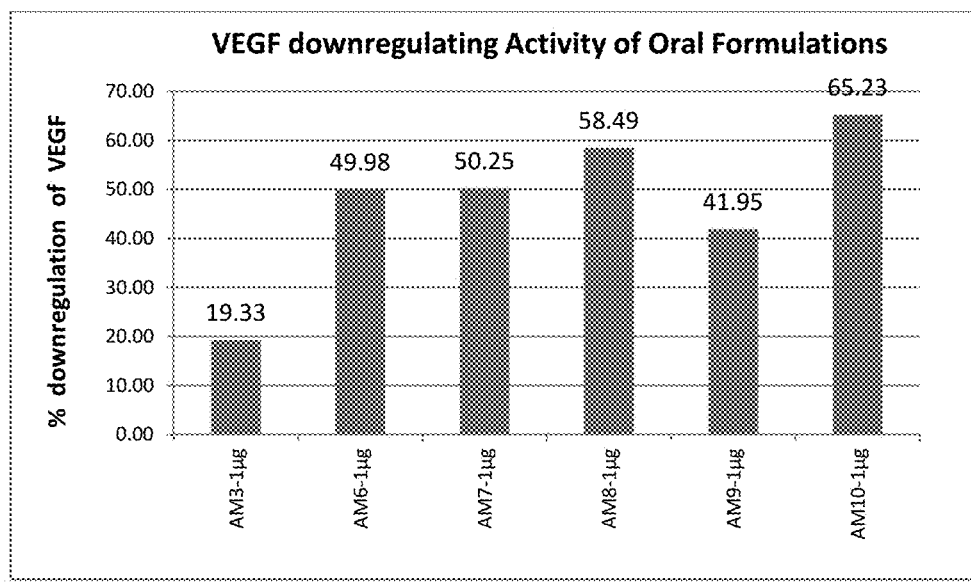
FIG. 1 depicts the VEGF down-regulating effect of different oral formulations in Human retinal pigmented epithelial (ARPE) cells.

The biological materials used in the present invention were collected from the following geographical locations: *Cinnamomum verum* was collected from Kerala. *Terminalia chebula* was collected from Kerala.

*Acacia catechu* was collected from Kerala.
*Silybum marianum* was collected from Kerala.
*Curcuma longa* was collected from Kerala.
*Punica granatum* was collected from Kerala.

DETAILED DESCRIPTION OF THE INVENTION

The term 'about' used herein refers to a marginal increase in the concentration of ±2% of the subject ingredient in the herbal composition of the present invention.

The term 'standardized extract' used herein refers to the extract comprising the phytochemical constituent in a specific concentration so as to exert therapeutic activity.

The invention will now be described in detail in connection with certain preferred and optional embodiments, so that various aspects thereof may be more fully understood and appreciated.

The present invention provides an herbal (s)/phytochemical (s) composition for the treatment of age related macular diseases (AMD). More specifically the present invention provides an herbal (s)/phytochemical (s) composition for the prevention, management and treatment of wet AMD and the prevention of the conversion of dry AMD to wet AMD.

In a preferred embodiment, the present invention provides an herbal anti-AMD composition comprising
(a) a standardized herbal extract (s) selected from the group consisting of *Cinnamomum verum, Terminalia chebula*, and *Acacia catechu* in concentrations constituting about 30% to about 50% of the present composition;
(b) a standardized herbal extract (s) selected from the group consisting of *Silybum marianum*, and *Curcuma longa*, in concentrations constituting about 20% to about 40% of the present herbal composition; and
(c) a standardized extract from *Punica granatum* constituting about 1% to about 10% of the present herbal composition.

In a general embodiment, the present invention provides an herbal composition comprising (a) herbal extract (s) selected from the group consisting of *Cinnamon* species, *Terminalia chebula* and *Acacia catechu* in concentrations constituting 0.1 to 50% of the present composition; (b) herbal extract (s) selected from the group consisting of *Silybum marianum* and *Curcuma longa* in concentrations constituting 0.1% to 40% of the present herbal composition; and (c) an extract from *Punica granatum* constituting 0.1% to 10% of the present herbal composition.

Accordingly, the said composition comprises extracts predominantly from the herbs selected from the group consisting of *Cinnamomum verum, Terminalia chebula*, and *Acacia catechu* in concentrations constituting about 30% to about 50% of the present composition.

Further, the present composition comprises extracts from the herbs selected from the group consisting of *Silybum marianum* and *Curcuma longa*, in concentrations constituting about 20% to about 40% of the present herbal composition.

Finally, the present herbal composition comprises an extract from *Punica granatum* constituting about 1% to about 10% of the composition.

The activity of the respective herbal extracts is conferred by the active ingredients of the herbal ingredients/extracts. Procyanidins from *cinnamon* bark extract, chebulinic acid and chebulagic acid from *T. chebula*, catechin from *A. catechu*, silymarin from *S. marianum*, curcumin and other curcuminoids from *Curcuma longa*, and ellagic acid from *Punica granatum*. The said active ingredients/phytochemicals belong to a group of polyphenols, flavonoids and glycoproteins.

In one more preferred embodiment, the present invention provides an herbal composition comprising 2 to 8% procyanidin derived from *cinnamon* bark extract, 8 to 25% chebulagic acid, and 15 to 30% chebulinic acid obtained from *Terminalia chebula*, 0.2 to 3% of catechin from *Acacia catechu*, 60 to 80% of silymarin from *S. marianum*, 35% to 100% of curcumin and/or curcuminoids from *Curcuma longa*, and 1 to 25% of ellagic acid from *Punica granatum*

In another preferred embodiment, the active ingredients from the extracts can be isolated, purified or synthesised and further developed either alone or in combination for the prevention/management/treatment of AMD and also enhancing the efficacy, reducing the frequency and dose of existing therapies. Accordingly, the active ingredients contained in the present composition are selected from chebulagic acid, chebulinic acid, catechin, anthocyanins, silymarin, curcumin and/or curcuminoids, lectins, ellagic acid, procyanidin, baicalin and wogonin.

The standardized herbal extract consisting of *Cinnamomum verum* comprises 2 to 8% procyanidin extracted from *C. verum*.

The standardized herbal extract consisting of *Terminalia chebula* comprises 8 to 25% chebulagic acid and 15 to 30% chebulinic acid obtained from *Terminalia chebula*;

The standardized herbal extract consisting of *Acacia catechu* comprises >3% of catechin extracted from *Acacia catechu*.

The standardized herbal extract consisting of *Silybum marianum* comprises up to 95% of silymarin extracted from *S. marianum*.

The standardized herbal extract consisting of *Curcuma longa* comprises 35% to 100% curcumin extracted from *C. longa*.

The standardized extract consisting of *Punica granatum* comprises 1 to 25% of ellagic acid which is extracted from *P. granatum*.

The aforesaid standardized extracts are prepared by conventional methods.

In an optional embodiment, the present invention provides an herbal composition comprising (a) herbal extract (s) selected from the group consisting of *Cinnamomum verum, Terminalia chebula*, and *Acacia catechu* in concentrations constituting about 30% to about 50% of the present composition; (b) optionally a herbal extract (s) selected from the group consisting of *Silybum marianum* and *Curcuma longa*, in concentrations constituting about 20% to about 40% of the present herbal composition; and (c) optionally an extract from *Punica granatum* constituting about 1% to about 10% of the present herbal composition.

In an embodiment, the present herbal composition can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, eye drops, solutions, suspensions, injections, gels and microspheres.

The present composition can be further developed as a nutraceutical formulation, ayurvedic preparation, food supplement or pharmaceutical drug.

Accordingly, the pharmaceutically acceptable excipients are selected from the group consisting of polymers, lubricants, buffer, chelating agent, wetting agents, surfactants, preservatives and diluents.

In accordance with the above, for oral formulation, (a) diluents used is micro-crystalline cellulose, sodium carboxymethylcellulose; (b) optional dispersing agent used is croscarmellose and povidone (c) lubricants used are silicon dioxide and magnesium stearate.

In accordance with the above, in ophthalmic formulation (a) the polymer used in the present composition is selected from hydroxyl propyl methyl cellulose (HPMC), micro-crystalline cellulose, sodium carboxymethylcellulose, (b) buffer is boric acid (borax), citrate, sodium chloride or phosphate buffer; (d) chelating agent is disodium edetate (e) wetting agents or solubility enhancers is selected from lecithin, soya lecithin, (f) surfactant used is selected from Tween 80 and D-α-Tocopherol polyethylene glycol succinate (TPGS) and (g) preservative used is benzyl alkonium chloride.

More importantly, the present composition can be formulated as oral dosage forms in the forms of tablets, capsules, suspensions, sachets etc. or topical ophthalmic dosage forms in the form of ocular gel, eye drops, stents, intra-vitreal injections, intra-vitreal stents and other relevant dosage forms.

In one preferred embodiment, the present invention provides an herbal anti-AMD formulation comprising;
  (i) a standardized herbal extract (s) selected from the group consisting of *Cinnamomum verum, Terminalia chebula*, and *Acacia catechu* in concentrations constituting about 30% to about 50% of the present composition;
  (ii) a standardized herbal extract (s) selected from the group consisting of *Silybum marianum* and *Curcuma longa* in concentrations constituting about 20% to about 40% of the present herbal composition; and
  (iii) a standardized extract from *Punica granatum* constituting about 1% to about 10% of the present herbal composition;
  (iv) one or more pharmaceutically acceptable excipients selected from polymers, lubricants, buffer, chelating agent, surfactants, preservatives, wetting agents and diluents.

The present herbal composition is formulated so as to allow the active ingredients contained therein to be bioavailable upon administration of the composition to a patient. Compositions that will be administered to a human subject or patient may take the form of one or more dosage units. The dosage forms can also be prepared as sustained, controlled, modified and immediate dosage forms.

In another preferred embodiment, the present invention provides an herbal composition for the prevention and/or stabilization, management and treatment of Age Related Macular Degeneration (AMD), specifically Wet-AMD.

Additionally, the present herbal composition is also employed in the prevention and/or stabilization, management and treatment of diabetic macular edema (DME) and retinal vein occlusion (RVO).

Accordingly, the said composition is employed in the treatment, prevention, stabilization, and also in adjunctive/adjuvant therapy for visual acuity loss in persons with newly diagnosed/early age-related macular degeneration, more specifically Wet-AMD. Specifically, the said composition can be used for the prevention of conversion of dry-AMD into Wet-AMD.

In one more preferred embodiment, the present invention provides a method of treating age related macular diseases in diseased individuals comprising administering a therapeutically effective concentration of the present herbal anti-AMD composition to a subject in need thereof.

Figure 2:
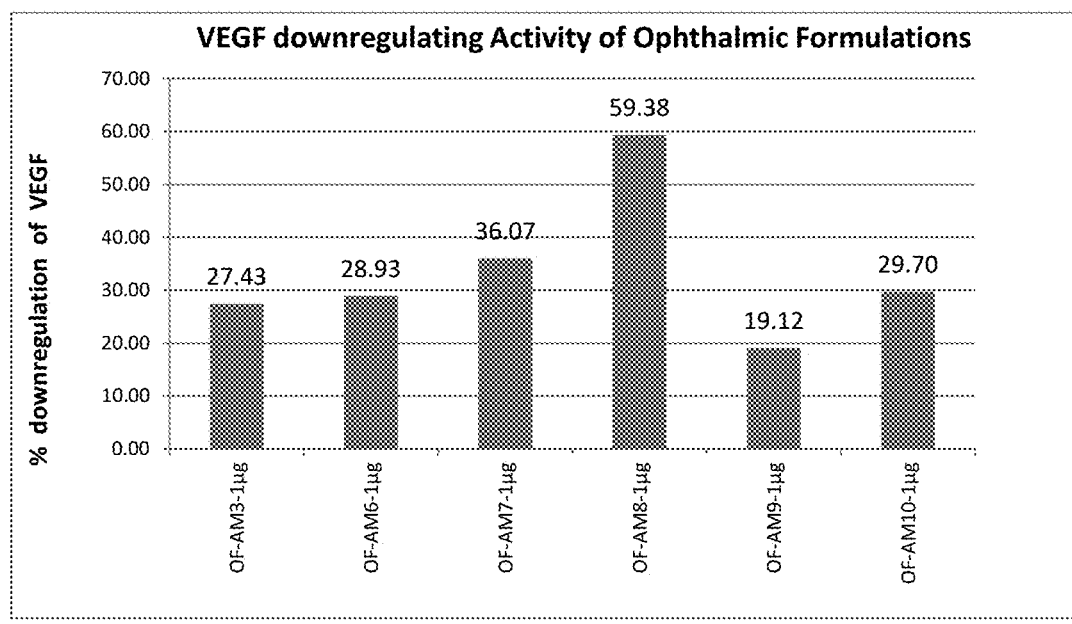
FIG. 2 depicts VEGF down-regulating effect of different ophthalmic formulations in ARPE cells.

The down regulation of the expression of VEGF, a causative agent of AMD was determined by administering the oral as well as ophthalmic formulations of the present invention. Each oral herbal formulation demonstrated down regulation of VEGF in ARPE cell lines. Percentage down regulation of VEGF was obtained with a minimum VEGF inhibition of 19.33% and maximum VEGF inhibition of 65.23% upon treatment with oral formulations (FIG. 1). Percentage down regulation of VEGF was observed at a minimum VEGF inhibition of 19.12% and a maximum VEGF inhibition of 59.38% upon treatment with ophthalmic formulations (FIG. 2). Each ophthalmic herbal formulation of the present invention demonstrated downregulation of VEGF in ARPE cell lines.

Figure 3:
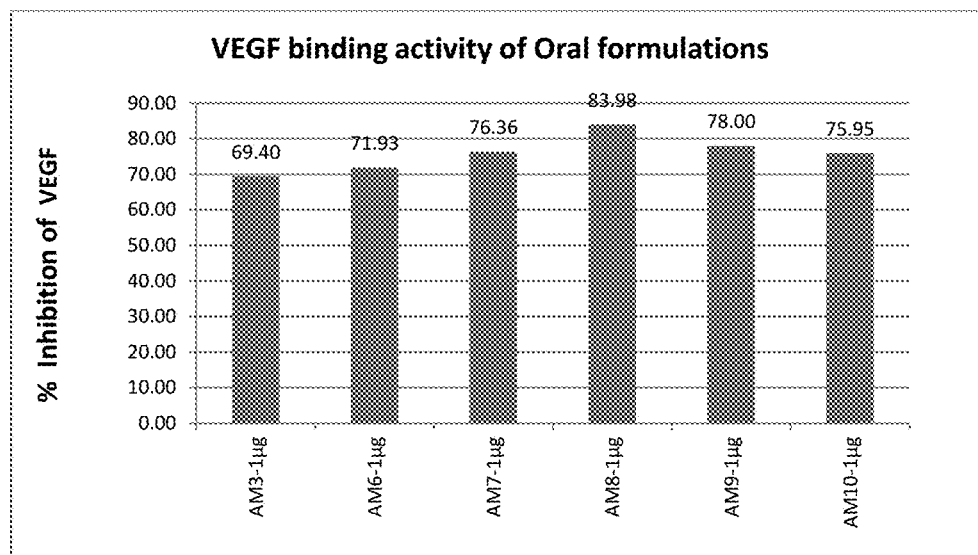
FIG. 3 depicts VEGF binding effect of different oral formulations in ARPE cells.
Figure 4:
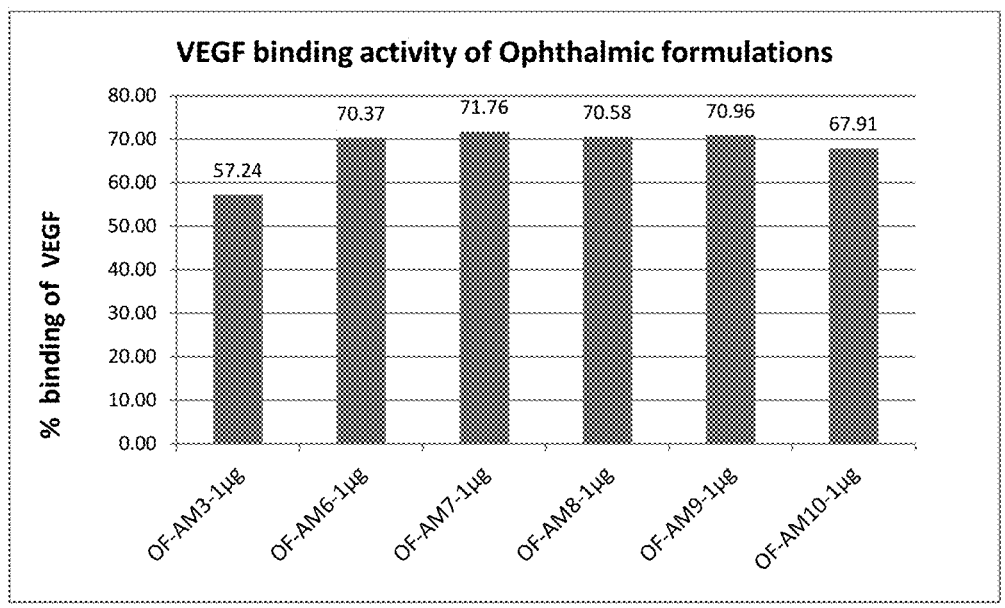
FIG. 4 depicts VEGF binding effect of different ophthalmic formulations in ARPE cells.

The inhibition/binding of VEGF was also determined for the oral and ophthalmic formulations of the present invention using ARPE cell lines. The percentage binding of VEGF was observed with a minimum VEGF inhibition of 64.4% and a maximum inhibition of 83.98% upon treatment with oral formulations (FIG. 3). Percentage binding of VEGF was observed to be in the range of 57% to 75% % upon treatment of ARPE cell lines with the ophthalmic formulation of the present invention (FIG. 4).

Further, tests were performed to determine the downregulation of VEGF followed by binding of VEGF in order to check the possible synergistic activity in real time. >90% change in VEGF was achieved using the present composition, i.e. both oral and ophthalmic formulations showed inhibitory activity of >90%.

Figure 7:
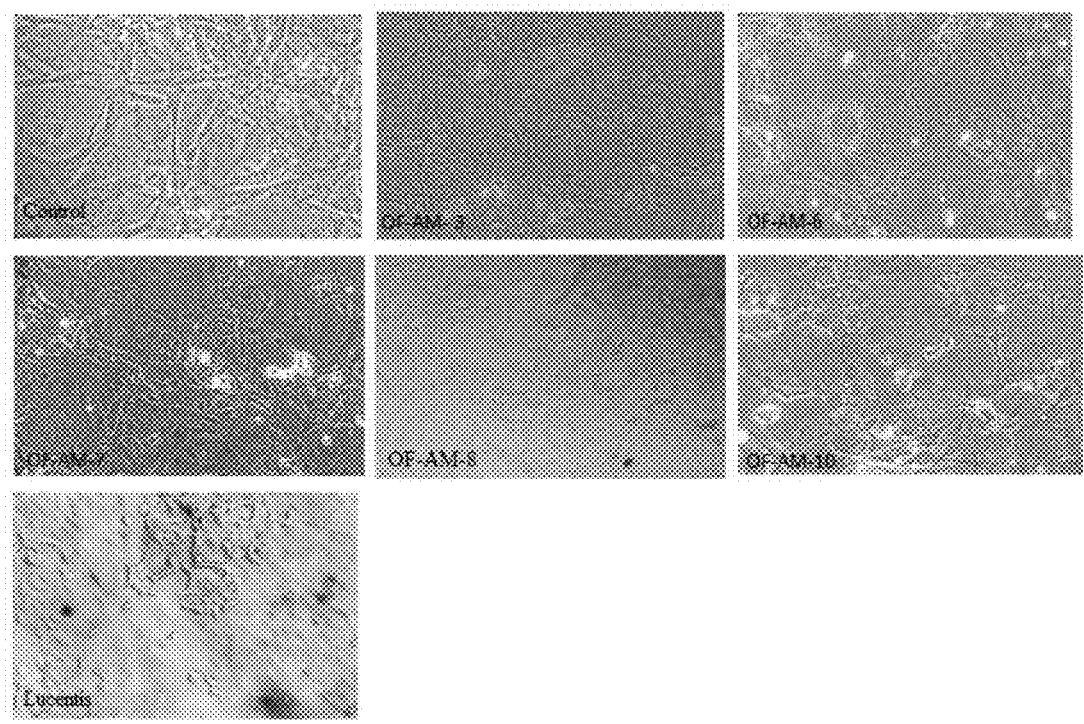
FIG. 7 depicts effect of treatment of different ophthalmic formulations on Angiogenesis of HUVEC cells, in comparison with control and Lucentis treatment.

The effect of the ophthalmic formulation comprising the present herbal composition on angiogenesis is depicted in FIG. 7. Experiments were carried out using ARPE cell lines and HUVEC cells. Half of the medium used for growth of the HUVEC cells were replaced with media obtained from induced ARPE cells grown in the presence of respective formulations at 1 µg/ml concentration. The angiogenesis in HUVEC's treated with the ophthalmic herbal composition of the present invention is inhibited to greater extent in ophthalmic compositions 8 and 10 (Example 4) and was comparable to Lucentis (Ranibizumab) treated cells under the experimental conditions. The inhibitory activity of the said compositions can be observed distinctly in FIG. 7.

Figure 8:
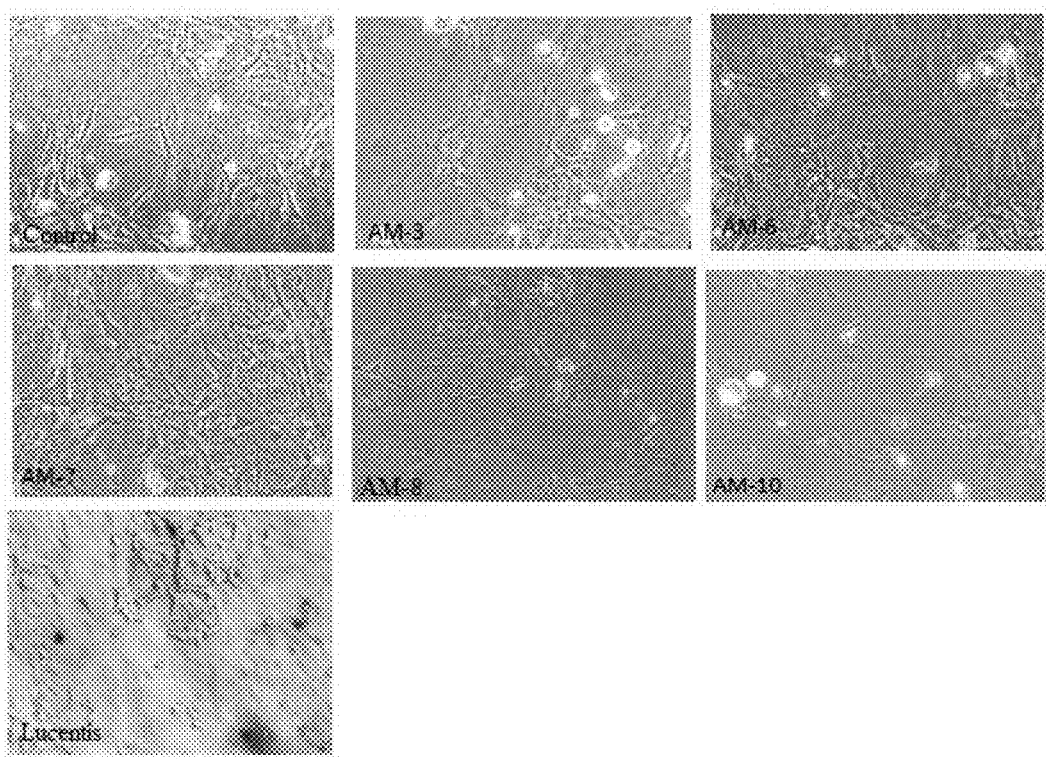
FIG. 8 depicts the effect of treatment of different oral formulations on Angiogenesis of HUVEC cells, in comparison with control and Lucentis treatment.

The effect of the oral formulation comprising the present herbal composition on angiogenesis is depicted in FIG. 8. The angiogenesis in HUVEC's treated with the oral herbal composition of the present invention is inhibited and is comparable to Lucentis (Ranibizumab) treated cells under the experimental conditions.

In another embodiment, the present invention can be used either alone or as an adjunct therapy to existing drugs/ biologics/biosimilars/bio-better/supplements/preventive measures/treatment measures. The said composition can be used in adjunct therapy/combination therapy for anti-VEGF's, siRNAs, anti-VEGF biologics/drugs, anti PDGF biologics/drugs and aminosterols such as squalamine, a matrix metalloproteinase inhibitors, AREDs formulations, lutein formulations, zeaxanthin formulation, meso-zeaxanthin formulation, astaxanthin formulations and mixtures thereof.

The said composition can be used for increasing the efficacy, reducing the dose and frequency of existing preventive and treatment therapy including drugs, biologics and supplements.

In an optional embodiment, the present herbal composition when co-administered with a biologic selected from ranibizumab, aflibercept, pegaptanib sodium and pazopanib enhances the efficacy of the said biologic.

Accordingly, the said composition can be used for increasing the efficacy and/or reducing the dose and frequency of intravitreal injections or enhancing the therapeutic efficacy of biologics such as ranibizumab, aflibercept, Pegaptanib Sodium, pazopanib etc. The present ophthalmic herbal composition comprising *Acacia catechu* extract, *Silybum marianum* extract and *Punica granatum* extract when administered along with Ranibizumab (Lucentis) exhibited increase in efficacy of the said biologic. Comparative analysis made available in FIG. 9 indicates an enhanced efficacy by 10% the VEGF binding ability of Ranibizumab when administered along with the present herbal composition.

The said composition can be used as post treatment management therapy and also to prevent the recurrence after treatment including Laser Photocoagulation treatment, drugs, biologics, supplements and other treatments The said composition can be used as either adjunct therapy and/combination therapy for intravitreal injection, ophthalmic topical dosage forms and oral dosage forms In one more preferred embodiment, the present invention provides an herbal composition having higher bioavailability to facilitate crossing blood and retinal barrier.

Advantages of the Present Composition:
Prevention, stabilization and/or treatment of visual acuity loss in persons with early age-related macular degeneration (AMD);
Increasing efficacy, reducing the dose and frequency of existing preventive and treatment therapy including drugs, biologics and supplements;
As a standalone product for the treatment and/or prevention of wet-AMD;
Prevention of conversion of dry-AMD into Wet-AMD
Additionally used in the treatment of visual loss in persons with diabetic macular edema (DME) and retinal vein occlusion (RVO).

The following examples, which include preferred embodiments, will serve to illustrate the practice of this invention, it being understood that the particulars shown are by way of example and for purpose of illustrative discussion of preferred embodiments of the invention.

EXAMPLES

Example 1: Formulation of the Herbal Composition

The actives and the herbs were procured from local sources. The actives were standardized and formulated into the present herbal composition. The herbal composition was formulated comprising 2 to 8% procyanidin/>30% Polyphenols derived from *cinnamon* bark extract, 8 to 25% chebulagic acid, and 15 to 30% chebulinic acid obtained from *Terminalia chebula*, 0.2 to 3% of catechin from *Acacia catechu*; up to 80%% of silymarin from *S. marianum*, 35% to 100% of curcumin and curcuminoids from *Curcuma longa*, and upto 95% of ellagic acid from *Punica granatum*. The herbal ingredients of the present formulation were standardized so as to obtain the aforesaid concentration of the phytochemical constituents.

TABLE 1

| Sl No | Group | Herbal extracts | Active ingredients | Concentration of active ingredient (s) |
|---|---|---|---|---|
| 1 | Group 1 | *Cinnamomum verum/ Cinnamonum cassia* bark extract | Procyanidins (polyphenols) | 2 to 8% procyanidin >30% Polyphenols |

TABLE 1-continued

| Sl No | Group | Herbal extracts | Active ingredients | Concentration of active ingredient (s) |
|---|---|---|---|---|
| | | *Terminalia chebula* | chebulinic acid, chebulagic acid (polyphenols) | 8-25% by weight chebulagic acid, 15-30% chebulinic acid, >30% polyphenols |
| | | *Acacia catechu* (black catechu) | Catechin (Flavonoids) | >3% w/w |
| | | Black Rice extract | Anthocyanins | >15% |
| 2 | Group 2 | *Silybum marianum* extract | Silymarin (Flavonoid) | >2% specifically (70-85% silymarin) |
| | | Turmeric extract | Curcumin, curcuminoids (polyphenols) | 35% to 100% |
| 3 | Group 3 | *Punica granatum* | Ellagic acid (polyphenol) | >25% (95% polyphenols) |

Example 2: Formulation of the Synthesized or Purified Phytochemical

The phytochemical constituents employed in the herbal composition of the present invention are contained in the Table herein below. The extracts obtained from the herbal extracts are standardized so as to contain a specific concentration of the phytochemicals.

TABLE 2

Composition can contain one or more phytochemical shown in the table below

| Sl No | Phytochemical | Herbal source |
|---|---|---|
| 1 | Procyanidins (polyphenols) | *Cinnamomum verum* |
| 2 | chebulinic acid, chebulagic acid (polyphenols) | *Terminalia chebula* |
| 3 | Baicalin (Flavonoids) and Wogonin | *Scutellaria baicalensis* |
| 4 | Procyanidins (polyphenols) | *Pinus pinaster* |
| 5 | Catechin (Flavonoids) | *Acacia catechu* |
| 6 | Silymarin (Flavonoid) | *S. marianum* |
| 7 | Curcumin, curcuminoids (polyphenols) | *Curcuma longa* |
| 8 | Ellagic acid (polyphenol) | *Punica granatum* |
| 9 | Anthocyanins | |

Example 3: Composition of Oral AMD Formulations

The compositions provided herein below comprised the extracts of herbal ingredients along with acceptable excipients for oral administration. The method of manufacturing the oral formulations employed was in accordance with conventional practices. The method for preparation of the following oral formulations in Tables 3 to 8 comprises the following steps:

a) The ingredients 1 to 3 were weighed and were mixed in a suitable mixture until a homogeneous mixture was obtained (~15 mins).
b) After mixing weighed quantity of de-oiled lecithin, MCC and Magnesium Stearate was incorporated one by one into the homogeneous mixture obtained in step (a) and further mixed for approximately 5 minutes after addition of each ingredient.
c) the powdered mixture obtained in step (b) was sieved using 40 micron mesh;
d) Sieved powdered mixture was filled in capsule using suitable capsule filling equipment.

TABLE 3

Composition of AM3

| Sl. No. | Ingredients | Quantity in g |
|---|---|---|
| 1. | *Terminalia chebula* fruit extract (50% Polyphenols) | 47 |
| 2. | *Curcuma longa* root extract (95% Curcuminoids) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Deoiled Lecithin | 1 |
| | Total | 100 |

TABLE 4

Composition of AM6

| Sl. No. | Ingredients | Quantity in g |
|---|---|---|
| 1. | *Cinnamomum verum* bark extract (50% Polyphenols) | 47 |
| 2. | *Silybum marianum* extract (80% Silymarin) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Deoiled Lecithin | 1 |
| | Total | 100 |

TABLE 5

Composition of AM7

| Sl. No. | Ingredients | Quantity in g |
|---|---|---|
| 1. | *Cinnamomum verum* bark extract (50% Polyphenols) | 47 |
| 2. | *Curcuma longa* root extract (95% Curcuminoids) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Deoiled Lecithin | 1 |
| | Total | 100 |

TABLE 6

Composition of AM8

| Sl. No. | Ingredients | Quantity in g |
|---|---|---|
| 1. | *Acacia catechu* extract (15% Catechin Flavonoid) | 47 |
| 2. | *Silybum marianum* extract (80% Silymarin) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Deoiled Lecithin | 1 |
| | Total | 100 |

TABLE 7

Composition of AM9

| Sl. No. | Ingredients | Quantity in g |
|---|---|---|
| 1. | *Terminalia chebula* fruit extract (50% Polyphenols) | 47 |
| 2. | *Silybum marianum* extract (80% Silymarin) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Lecithin | 1 |
| | Total | 100 |

TABLE 8

Composition of AM10

| Sl. No. | Ingredients | Quantity in g |
|---|---|---|
| 1. | *Acacia catechu* extract (15% Catechin Flavonoid) | 47 |
| 2. | *Curcuma longa* root extract (95% Curcuminoids) | 39 |
| 3. | *Punica granatum* extract (95% Polyphenols) | 8 |
| 4. | Micro Crystalline Cellulose (MCC) | 3 |
| 5. | Magnesium Stearate | 2 |
| 6. | Deoiled Lecithin | 1 |
| | Total | 100 |

Example 4: Composition of Ophthalmic AMD Formulation

The following ophthalmic formulations comprise the herbal ingredients mentioned in corresponding oral compositions mentioned in Example 3. Each table herein below provides ophthalmic formulations comprising extracts of the said herbal ingredients along with excipients.

TABLE 9

Composition of Ophthalmic (OF)-AM3

| Sl. No. | Ingredients | Quantity (g) for 100 ml (Weight/Volume) |
|---|---|---|
| 1 | *Terminalia chebula* fruit extract (50% Polyphenols) | 0.031 |
| 2 | *Curcuma longa* root extract (95% Curcuminoids) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |
| 9 | EDTA Disodium | 0.010 |
| 10 | Sodium Chloride | 0.790 |
| 11 | Distilled Water | 95.086 |

TABLE 10

Composition of OF-AM6

| Sl. No. | Ingredients | Quantity (g) for 100 ml (Weight/Volume) |
|---|---|---|
| 1 | *Cinnamomum verum* bark extract (50% Polyphenols) | 0.031 |
| 2 | *Silybum marianum* extract (80% Silymarin) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |
| 9 | EDTA Disodium | 0.010 |
| 10 | Sodium Chloride | 0.790 |
| 11 | Distilled Water | 95.086 |

TABLE 11

Composition of OF-AM7

| Sl. No. | Ingredients | Quantity (g) for 100 ml (Weight/Volume) |
|---|---|---|
| 1 | *Cinnamomum verum* bark extract (50% Polyphenols) | 0.031 |
| 2 | *Curcuma longa* root extract (95% Curcuminoids) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |
| 9 | EDTA Disodium | 0.010 |
| 10 | Sodium Chloride | 0.790 |
| 11 | Distilled Water | 95.086 |

TABLE 12

Composition of OF-AM8

| Sl. No. | Ingredients | Quantity (g) for 100 ml (Weight/Volume) |
|---|---|---|
| 1 | *Acacia catechu* extract (15% Catechin Flavonoid) | 0.031 |
| 2 | *Silybum marianum* extract (80% Silymarin) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |

TABLE 12-continued

Composition of OF-AM8

| Sl. No. | Ingredients | Quantity (g) for 100 ml (Weight/Volume) |
|---|---|---|
| 9 | EDTA Disodium | 0.010 |
| 10 | Sodium Chloride | 0.790 |
| 11 | Distilled Water | 95.086 |

TABLE 13

Composition of OF-AM9

| Sl. No. | Ingredients | Quantity (g) for 100 ml (Weight/Volume) |
|---|---|---|
| 1 | *Terminalia chebula* fruit extract (50% Polyphenols) | 0.031 |
| 2 | *Silybum marianum* extract (80% Silymarin) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |
| 9 | EDTA Disodium | 0.010 |
| 10 | Sodium Chloride | 0.790 |
| 11 | Distilled Water | 95.086 |

TABLE 14

Composition of OF-AM10

| Sl. No. | Ingredients | Quantity (g) for 100 ml (Weight/Volume) |
|---|---|---|
| 1 | *Acacia catechu* extract (15% catechin Flavonoid) | 0.031 |
| 2 | *Curcuma longa* root extract (95% Curcuminoids) | 0.025 |
| 3 | *Punica granatum* extract (95% Polyphenols) | 0.005 |
| 4 | Tween 80 | 3.421 |
| 5 | TPGS | 0.489 |
| 6 | Hydroxypropyl methylcellulose | 0.100 |
| 7 | Borax | 0.023 |
| 8 | Benzyl-alkonium chloride | 0.020 |
| 9 | EDTA Disodium | 0.010 |
| 10 | Sodium Chloride | 0.790 |
| 11 | Distilled Water | 95.086 |

Example 5: VEGF Down-Regulation

Effect of these formulations in down-regulating the VEGF production was assessed by using Human retinal pigment epithelial (ARPE) cell lines. ARPE cells were treated using these formulations at 1 µg/ml concentration and after incubation, media collected and checked for VEGF expression using Human VEGF ELISA kit (Merck, Millipore). Results affirmed that all the formulations tested have VEGF down-regulating activity (FIG. 1 and FIG. 2). Percentage down regulation of VEGF was observed with a minimum VEGF inhibition of 19.33% and maximum VEGF inhibition of 65.23% upon treatment with oral formulations as observed in FIG. 1. Each oral herbal formulation demonstrated in Example 3 showed downregulation of VEGF in ARPE cell lines. Percentage down regulation of VEGF was observed with a minimum VEGF inhibition of 19.12% to a maximum VEGF inhibition of 59.38% upon treatment with ophthalmic formulations as observed in FIG. 2. Each ophthalmic herbal formulation demonstrated in Example 4 showed downregulation of VEGF in ARPE cell lines

Example 6: VEGF Binding Efficacy

Effect of these formulations in binding VEGF was assessed by using ARPE cell lines. ARPE cells were cultured to produce VEGF with inducer. After incubation, media collected and treated with test substance at 1 µg/ml concentration and estimated for VEGF using Human VEGF ELISA kit (Merck, Millipore). Results affirmed that all the formulations tested have VEGF binding activity (FIG. 3 & FIG. 4). Percentage binding of VEGF was observed with a minimum VEGF binding of 64.4% and a maximum binding of 83.98% upon treatment with oral formulations. Percentage binding of VEGF was observed with a minimum of 57.24% to a maximum of 71.76% upon treatment of induced ARPE cell line media containing VEGF with the ophthalmic formulation of the present invention.

Example 7: Synergistic VEGF Down-Regulation and Binding

Figure 5:
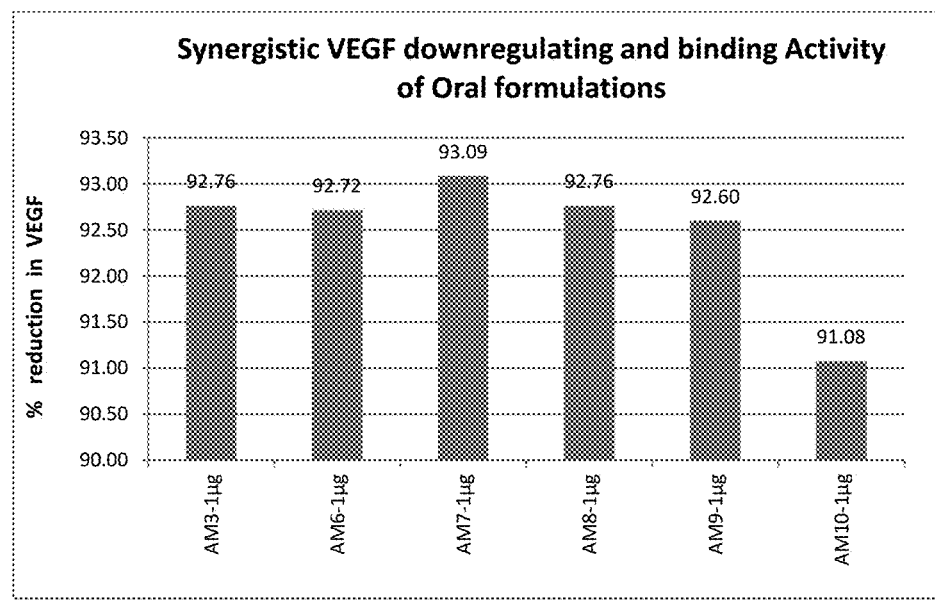
FIG. 5 depicts synergistic VEGF down-regulating and binding effect of different oral formulations in ARPE cells.
Figure 6:
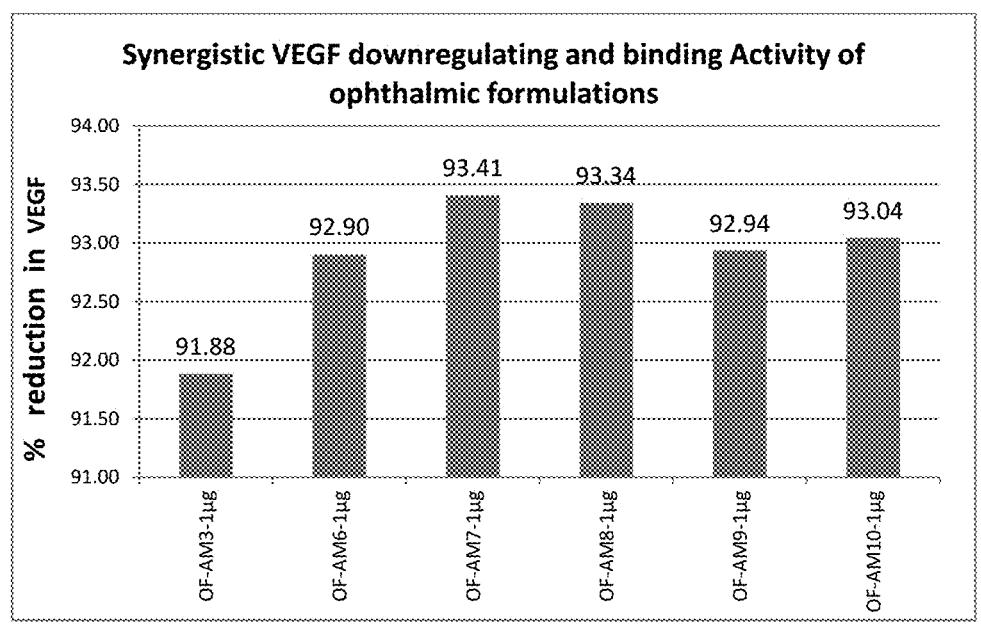
FIG. 6 depicts synergistic VEGF down-regulating and binding effect of different ophthalmic formulations in ARPE cells.

Effect of these formulations in synergistically down-regulating and binding released VEGF was assessed by using ARPE cell lines. Induced ARPE cells were treated using the present formulations demonstrated in Examples 3 and 4 at 1 µg/ml concentration and after incubation, media collected (to check VEGF down-regulation effect) and treated again with test substance at 1 µg/ml concentration (to check VEGF binding effect) and estimated for VEGF expression using Human VEGF ELISA kit (Merck, Millipore). Results affirmed that all the formulations tested synergistically act to down-regulate and bind VEGF (FIG. 5 & FIG. 6). Percentage reduction in VEGF was observed with a minimum of 91.08% to a maximum of 93.09% upon treatment of oral formulations. Percentage reduction in VEGF was observed with a minimum of 91.88% to a maximum of 93.41% upon treatment of ophthalmic formulations.

Example 8: Inhibition of Angiogenesis

Effect of these formulations in inhibition of angiogenesis was assessed by using Human Umbilical Vein Endothelial Cells (HUVEC). Half of the medium used for growth of the HUVEC cells were replaced with media obtained from induced ARPE cells grown in the presence of respective formulations at 1 µg/ml concentration. Media obtained from induced ARPE cells were added to control HUVEC cell group. Lucentis were added at 1 ng/ml concentration to induced ARPE media (obtained from induced ARPE cell lines) which forms 50% of the media. After incubation, all the cells from each group were observed for presence of angiogenesis (FIGS. 7 & 8) under microscope. In all treatment group inhibition of angiogenesis was observed. Ophthalmic formulations (OF) OF-AM-8, OF-AM-10, and oral formulations AM-8 and AM-10 were found to have significant angiogenesis inhibitory activity and were observed to have comparable reduction in angiogenesis to that of Lucentis.

Example 9: Synergistic Activity of OF-AM-8 with Lucentis (Ranibizumab) Indicating the Enhancement of Efficacy of Lucentis by OF-AM-08

Synergistic efficacy of OF-AM-8 with Lucentis (Ranibizumab) or efficacy enhancement of Lucentis by OF-AM-8 was evaluated in induced ARPE cell lines followed by VEGF analysis.

Figure 9:
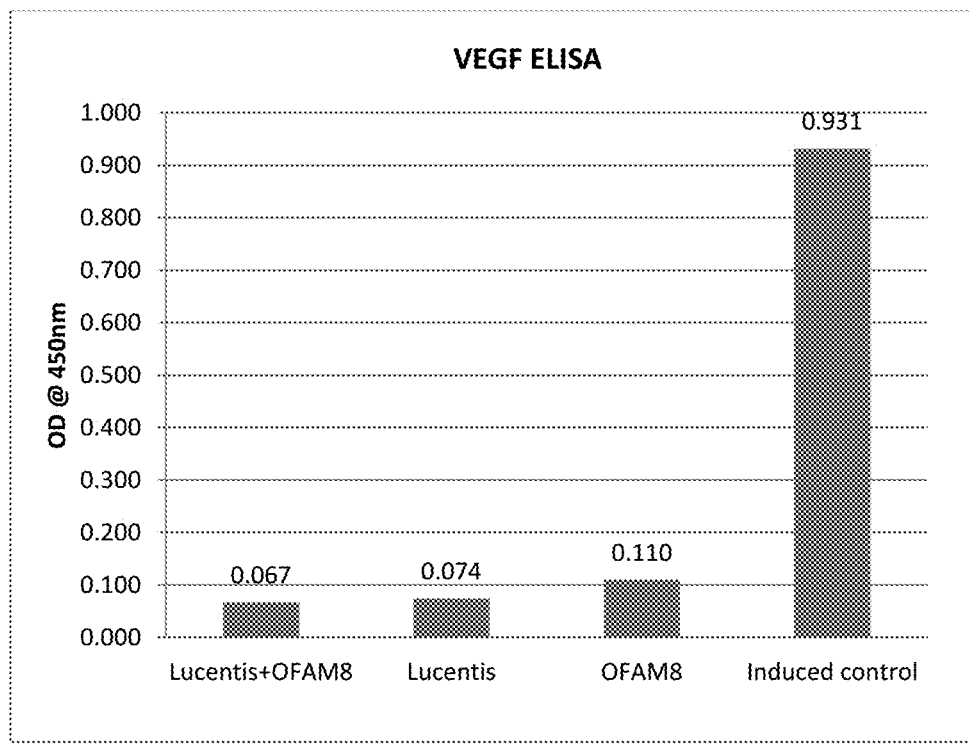
FIG. 9 depicts the synergistic activity of OF-AM-8 with Lucentis (Ranibizumab)/Enhancement of efficacy of Lucentis by OF-AM-08 when compared to Lucentis alone.

Induced ARPE cells were treated using OF-AM-8 formulation (Table 12 in Example 4) at 100 ng/ml concentration and after incubation, media was collected and estimated for VEGF using Human VEGF ELISA kit (Merck, Millipore). The collected media was treated again with Lucentis at 0.5 ng/ml concentration and estimated for VEGF, after incubation using Human VEGF ELISA kit (Merck, Millipore). In similar way, the media from induced untreated ARPE cells was collected, treated with Lucentis and estimated for VEGF, after incubation using Human VEGF ELISA kit (Merck, Millipore). Media from induced ARPE cells were also tested for VEGF concentration. Results affirmed that OF-AM-8 synergistically acts with Lucentis and enhance the efficacy of Lucentis (FIG. 9). There was about 10% increase in efficacy of Lucentis in the presence of OF-AM-8 when compared to Lucentis alone.

We claim:

1. An herbal anti-age related macular disease corn position which downregulates VEGF protein/activity and PDGF protein/activity in a subject comprising (a) an extract of *Acacia catechu* in an amount of 40% to 50% by weight of the composition; (b) an extract of *Silybum marianum* in an amount of 30% to 40% by weight of the composition; and (c) an extract of *Punica granatum* in an amount of 1% to 10% by weight of the composition.

2. The herbal composition according to claim 1, comprising at least one pharmaceutically acceptable excipient selected from the group consisting of polymers, diluents, lubricants, buffers, dispersing agents, chelating agents, wetting agents, surfactants and preservatives.

3. The herbal composition according to claim 2, wherein the composition is an oral formulation or an ophthalmic formulation.

4. An ophthalmic formulation comprising the herbal anti-age related macular disease composition according to claim 1, said ophthalmic formulation further comprising at least one of:
   a) a polymer selected from the group consisting of hydroxypropyl methyl cellulose, sodium carboxymethylcellulose and a mixture thereof;
   b) a surfactant selected from the group consisting of polysorbate 80, α-tocopherol polyethylene glycol succinate and a mixture thereof;
   c) disodium edetate; and
   d) benzyl alkonium chloride
said ophthalmic formulation being a liquid or gel.

5. A method of treating an age related macular disease in a subject in need thereof comprising administering a therapeutically effective amount of the herbal anti-age related macular disease composition of claim 1 to said subject.

6. The method of claim 5, wherein the herbal anti-age related macular disease composition is administered in conjunction with the administration of at least one Ranibizumab, Aflibercept, Pegaptanib Sodium and Pazopanib.

* * * * *